United States Patent
Hallock et al.

[19]

[11] Patent Number: 6,133,501
[45] Date of Patent: *Oct. 17, 2000

[54] ABSORBENT ARTICLE WITH RETAINING STRUCTURE FOR RECEIVING AND RETAINING FECAL MATERIAL

[75] Inventors: Roxanne Belinda Hallock, Oshkosh, Wis.; Dede Anne Cooke, Minnetonka, Minn.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/738,956

[22] Filed: Oct. 24, 1996

[51] Int. Cl.$^7$ .................................................. A61F 13/15
[52] U.S. Cl. ........................ 604/369; 604/378; 604/381; 604/385.19; 604/385.24
[58] Field of Search ...................... 604/348, 369, 604/380–81, 385.1, 385.2, 387, 397–402, 378, 385.01, 385.08, 385.101, 385.19, 385.24

[56] References Cited

U.S. PATENT DOCUMENTS

| | | | |
|---|---|---|---|
| 2,690,749 | 10/1954 | Nelson | 604/398 |
| 4,413,996 | 11/1983 | Taylor | 604/382 |
| 4,501,587 | 2/1985 | Enloe . | |
| 4,610,679 | 9/1986 | Matsushita | 604/369 |
| 4,610,682 | 9/1986 | Kopp . | |
| 4,657,539 | 4/1987 | Hasse | 604/385.2 |
| 4,662,877 | 5/1987 | Williams . | |
| 4,731,065 | 3/1988 | Yamada | 604/355 |
| 4,778,459 | 10/1988 | Fuisz | 604/378 |
| 4,781,713 | 11/1988 | Welch et al. | 604/385.1 |
| 4,828,555 | 5/1989 | Hermansson | 606/379 |
| 4,892,536 | 1/1990 | DesMarais et al. | 604/385.2 |
| 4,968,312 | 11/1990 | Khan | 604/388.1 |
| 4,988,344 | 1/1991 | Reising et al. | 604/368 |
| 4,988,345 | 1/1991 | Reising | 604/368 |
| 4,994,052 | 2/1991 | Kimura | 604/355 |
| 5,062,840 | 11/1991 | Holt et al. | 604/385.1 |
| 5,134,007 | 7/1992 | Reising et al. | 428/78 |
| 5,171,236 | 12/1992 | Dreier et al. | 604/369 |
| 5,176,672 | 1/1993 | Bruemmer et al. | 604/385.1 |
| 5,207,662 | 5/1993 | James | 604/385.2 |
| 5,211,641 | 5/1993 | Roos et al. | 604/385.1 |

(List continued on next page.)

FOREIGN PATENT DOCUMENTS

| | | | |
|---|---|---|---|
| 05 61023 | 9/1993 | European Pat. Off. | 604/385.2 |
| 0 585 904 | 3/1994 | European Pat. Off. . | |
| 2 495 899 | 6/1982 | France . | |
| 2 561 078 | 9/1985 | France . | |
| 2 573 629 | 5/1986 | France . | |
| 1298527 | 4/1971 | United Kingdom . | |
| 2074875 | 11/1981 | United Kingdom . | |
| 2296192 | 6/1996 | United Kingdom . | |
| 93/25172 | 12/1993 | WIPO . | |
| 95/27459 | 10/1995 | WIPO . | |
| 95/32698 | 12/1995 | WIPO . | |
| 96/21409 | 7/1996 | WIPO . | |
| 97/16144 | 5/1997 | WIPO . | |

*Primary Examiner*—John G. Weiss
*Assistant Examiner*—K. M. Reichle
*Attorney, Agent, or Firm*—Michael L. Winkelman; Jeffrey B. Curtin

[57] ABSTRACT

An absorbent article includes an outer cover, a bodyside liner and an absorbent core. A fecal retaining structure defines a perimeter having an aperture therein. The fecal retaining structure includes channels extending outwardly from the aperture. The fecal retaining structure preferably includes a cavity about the perimeter thereof and in communication with the channels. The cavity preferably communicates with the channels and provides additional volume for storage of fecal material. The fecal retaining structure preferably is formed by two layers of resiliently compressible material having different rigidity and compression resistance. One of the layers is smaller than the other layer such that space to form the cavity is present inside the fecal retaining structure. In a preferred embodiment the fecal retaining structure has a bicycle-seat shape with the narrow front portion extending into the front portion of the absorbent article.

11 Claims, 5 Drawing Sheets

U.S. PATENT DOCUMENTS

| | | | |
|---|---|---|---|
| 5,269,775 | 12/1993 | Freeland et al. | 604/385.2 |
| 5,300,053 | 4/1994 | Genaro | 604/378 |
| 5,306,266 | 4/1994 | Freeland | 604/385.1 |
| 5,330,459 | 7/1994 | Lavon et al. | 604/385.1 |
| 5,334,177 | 8/1994 | Cohen | 604/378 |
| 5,342,338 | 8/1994 | Roe | 604/383 |
| 5,366,453 | 11/1994 | Zehner et al. | 604/385.2 |
| 5,417,680 | 5/1995 | Kimura et al. | 604/385.2 |
| 5,451,442 | 9/1995 | Pieniak et al. | 428/54 |
| 5,613,961 | 3/1997 | DiPalma et al. | 604/385.2 |
| 5,624,423 | 4/1997 | Anjur et al. | 604/385.2 |
| 5,649,918 | 7/1997 | Schleinz | 604/385.2 |
| 5,807,367 | 9/1998 | Dilnik | 604/385.2 |

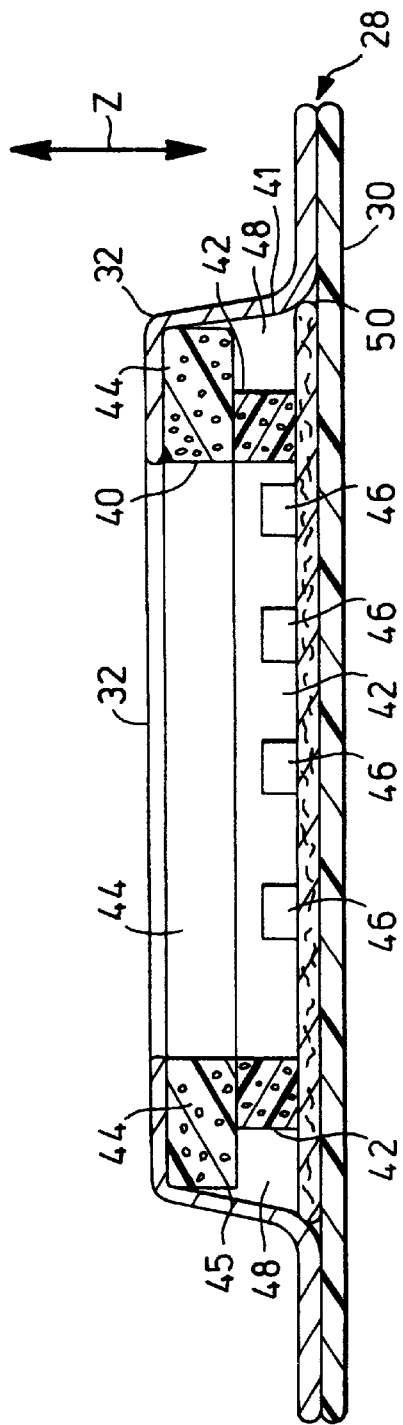
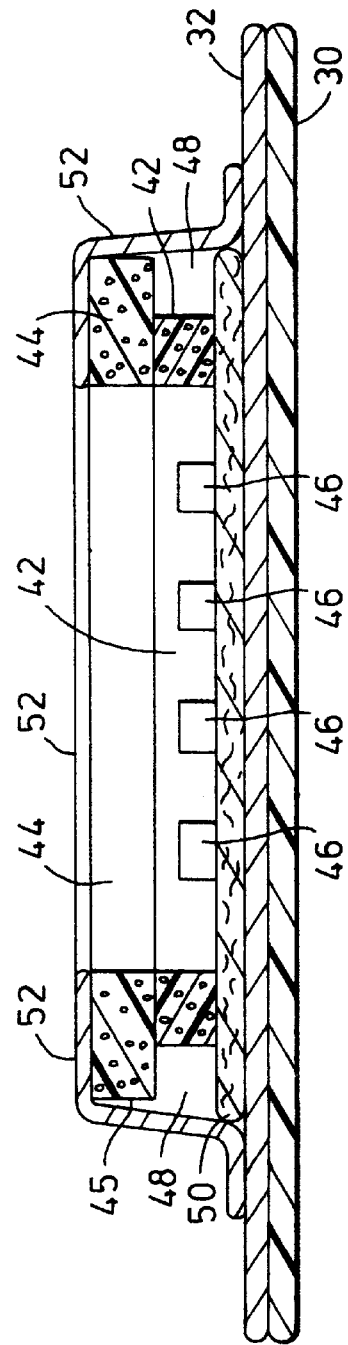

ABSORBENT ARTICLE WITH RETAINING STRUCTURE FOR RECEIVING AND RETAINING FECAL MATERIAL

FIELD OF THE INVENTION

Absorbent articles such as infant diapers, training pants, adult incontinence products, and the like are well known. Such articles have achieved a wide acceptance due to their ability to receive and absorb body exudates.

BACKGROUND OF THE INVENTION

In general, body exudates of urine, fecal, and similar materials should be received and contained by the absorbent article. However, leakage problems are common, especially leakage of fecal material. Furthermore, even if exudates do not leak, they can have an adverse impact on the skin of a user of an absorbent article because of contact between exudates and the buttocks and other areas of the body within the absorbent article.

Currently, absorbent articles find wide spread use in infant and adult incontinence care, and have generally replaced reusable or washable cloth absorbent articles. A typical absorbent article is a threelayered composite structure comprising a liquid-permeable topsheet, a liquid-impermeable backsheet, an absorbent assembly between the topsheet and the backsheet, and a fastener for securing the article to the wearer.

U.S. Pat. No. 5,330,459 to Lavon et al discloses an absorbent article having an inflatable spacer 210 which inflates when contacted by water to create a void space for exudates.

U.S. Pat. No. 5,176,672 to Bruemmer et al discloses an absorbent article having a cleft block 26 and a pledget 20. A superabsorbent material can surround the hole or aperture. The superabsorbent material can increase the size of the hole when liquid swells the material.

U.S. Pat. No. 4,731,065 to Yamada discloses a sanitary napkin having a recess in an absorbent element 11. The recess is formed of water-permeable paper 16 such as synthetic fiber paper.

SUMMARY OF THE DISCLOSURE

In the present invention, an absorbent article isolates and minimizes contact of exudate material with the skin. The absorbent article has a length and a width, a front portion and a rear portion, and a central axis perpendicular to the length of the absorbent article and dividing the absorbent article into the front portion and the rear portion. The absorbent article comprises a chassis comprising an outer cover and a bodyside liner mounted to the outer cover and contacting the body of the user. An absorbent core is located between the bodyside liner and the outer cover. A fecal retaining structure is mounted to the chassis at least in the rear portion of the absorbent article. The fecal retaining structure has at least one layer of a resiliently compressible material defining a perimeter of the fecal retaining structure, and encompassing an aperture in the fecal retaining structure. The resiliently compressible material has sufficient flexibility to press and seal against the body of a user when bent during application to the body of the user and sufficient compression resistance to maintain space in the aperture about the anus of a user under normal application of weight and pressure of the user.

In most embodiments the absorbent core is laterally displaced from the fecal retaining structure. In most embodiments, a layer of cellulosic material is secured to the chassis between the chassis and the fecal retaining structure. The layer of cellulosic material preferably comprises an uncreped through-air dried layer.

In most embodiments, the layer of resiliently compressible material is substantially free from superabsorbent material, is non-pneumatic, and preferably comprises a resiliently compressible foam material. The layer of resiliently compressible material preferably extends about the entire circumference of the aperture. The layer of resiliently compressible material can comprise closed cell polyethylene foam or polypropylene foam.

In some embodiments, the compressibility of the resiliently compressible material increases with increasing distance of the resiliently compressible material away from the body facing surface of the fecal retaining structure, thereby defining a compressibility gradient.

In some embodiments there are two layers of resiliently compressible material. A first layer has a first compressibility. A second layer of resiliently compressible material is spaced outwardly from the first layer and is placed adjacent the body of the user. The second layer has a second compressibility. The first compressibility is different than, and preferably less than, the second compressibility.

In most embodiments, channels are formed in the layer and extend radially outwardly of the aperture. In most embodiments, the fecal retaining structure is capable of storing at least 90 cubic centimeters of exudates. A front edge of the fecal retaining structure extends from about 1.2 centimeters to about 5 centimeters frontwardly of the central axis and into the front portion.

In some embodiments, the fecal retaining structure has an uncompressed thickness of between about 1.2 centimeters and about 2.5 centimeters at rest. The fecal retaining structure has a length and a width, the length of the fecal retaining structure can be about 45% to about 65% of the length of the absorbent article at rest.

In some embodiments, the perimeter of the fecal retaining structure is overlain by a layer of liquid impermeable material, the liquid impermeable material separating exudates in channels from the skin of the user. The fecal retaining structure can have a wide variety of shapes, including elliptical shapes or rectangular shapes.

In some embodiments, the bodyside liner separates the layer of resiliently compressible material from the body of the user. The bodyside liner is located about the aperture and is impermeable to liquid along the perimeter of the fecal retaining structure.

In another embodiment of the invention the fecal retaining structure has channels communicating with the aperture. The channels preferably extend outwardly of the aperture of the fecal retaining structure. The channels preferably have a length of from about 1.9 centimeters to about 4.5 centimeters. The channels preferably have a width of from about 0.6 centimeters to about 1.9 centimeters. The channels communicate with each other at outwardly disposed channel ends about a perimeter of the fecal retaining structure. The channels preferably number from about 6 to about 22. At least two channels extend to a common cavity receiving and storing fecal material away from the skin of the user.

In some embodiments the fecal retaining structure has a perimeter overlain by a layer of liquid and fecal impermeable material. The liquid impermeable material separates exudates in the channels from the skin of a user.

In some embodiments the fecal retaining structure has a bicycle-seat shape comprising a narrow portion and a wide portion, at least part of the narrow portion being disposed in the front portion of the absorbent article and the wide portion being disposed in the rear portion of the absorbent article.

BRIEF DESCRIPTION OF THE DRAWINGS

FIG. 5 shows a cross section of the absorbent article taken at 5—5 of FIG. 1.

FIG. 7 shows a cross section of the absorbent article taken at 7—7 of FIG. 6.

Figure 1:
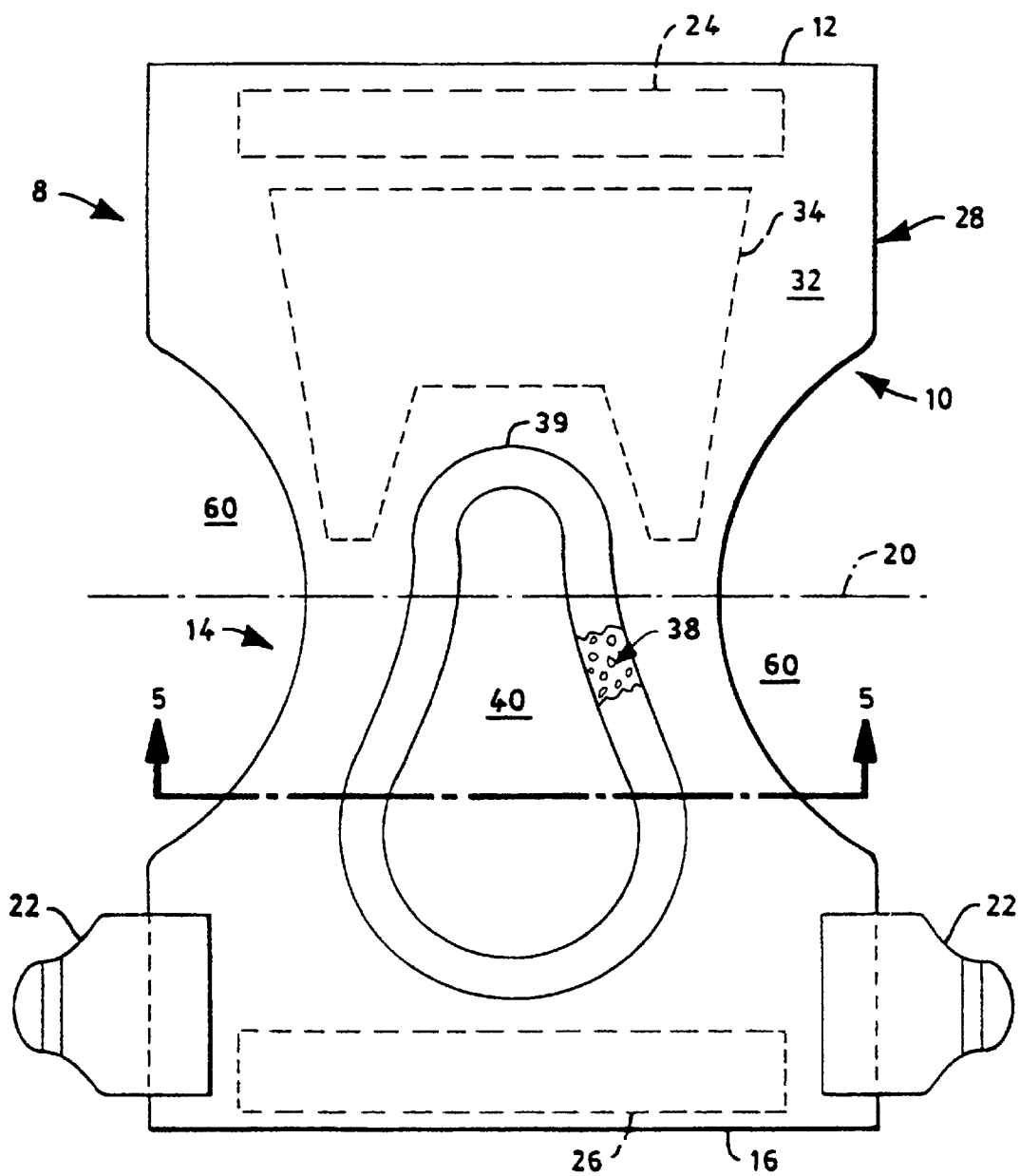
FIG. 1 shows a top view, with a partial section, of the inner or body side of an absorbent article of the invention.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

The absorbent article 8 shown in FIG. 1 includes a front portion 10 having a front edge 12, and a rear portion 14 having a rear edge 16. A transverse central axis 20, extends across the width of the absorbent article between front portion 10 and rear portion 14. Front and rear portions 10,14 have substantially equal lengths in the longitudinal direction of absorbent article 8. Attachment ears 22 secure absorbent article 8 to the body of a user. Front waist elastomeric element 24 and rear waist elastomeric element 26 provide proper tension for absorbent article 8 when secured to the body of the user.

A chassis 28 is formed by an outer cover 30, shown in FIG. 5, and a bodyside liner 32. Absorbent core 34, shown in FIG. 1, receives and retains liquid exudates. A fecal retaining structure 38 having an aperture 40 receives and retains fecal material expelled from the body of the user. First and second layers of compressible material 42, 44, shown in FIGS. 3–5 and 7, are part of fecal retaining structure 38. Channels 46 in first layer 42 allow fecal material to enter cavity 48 shown in FIG. 5. A layer of cellulosic pulp 50, shown in FIG. 5, absorbs and retains liquids from fecal material.

Figure 2:
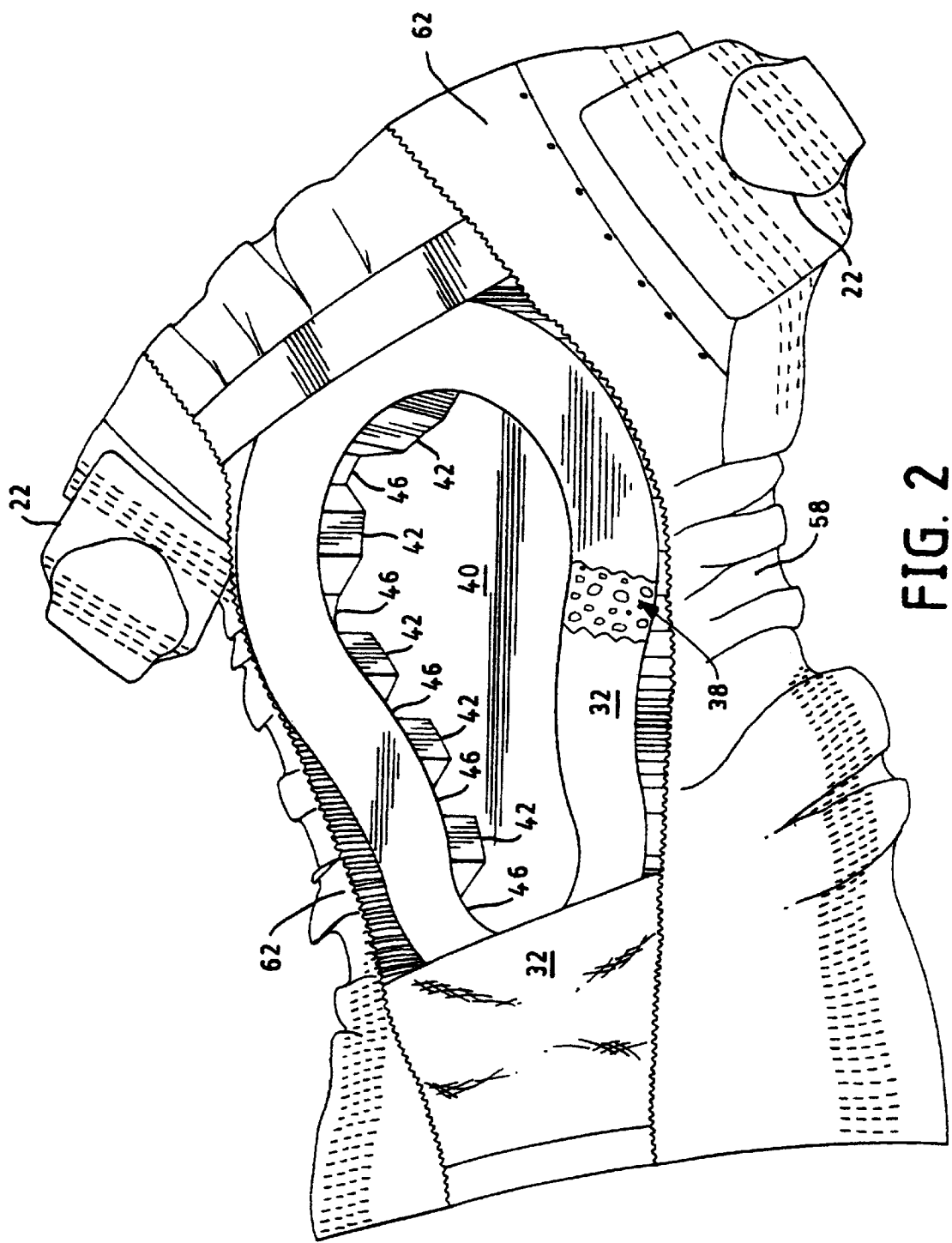
FIG. 2 shows an angled view, with a partial section, of an absorbent article similar to FIG. 1 with additional elements including leg cuffs and containment flaps.

Leg cuffs 58, shown in FIG. 2, place tension across leg cut-outs 60 of absorbent article 8. Containment flaps 62 provide a visual assurance to the user that absorbent article 8 will not leak.

Absorbent article 8 in FIG. 1 is applied to the body of the user by securing attachment ears 22 from rear portion 14 to a securement surface (not shown) on outer cover 30 of front portion 10. Attachment ears 22 can comprise the hooks of a hook and loop fastening system. The securement surface then typically comprises a corresponding loop material attached to outer cover 30 in front portion 10 and adapted to releasably engage with the hook material. Other well known fastening means can also be used to support absorbent article 8 upon the user. For example, a cohesive system, an adhesive fastener system or the like may also be utilized to secure absorbent article 8 to the body of the user.

Front waist elastomeric element 24 and rear waist elastomeric element 26 provide retractive forces urging retainment of absorbent article 8 to the body of the user. Elastomeric elements 24, 26 can be formed from materials which are attached to outer cover 30 and/or bodyside liner 32 of chassis 28. Suitable materials include strands or ribbons, or one or more layers of polymeric and/or elastomeric material which may be adhered or otherwise mounted to absorbent article 8 while in a stretched position. Alternatively, the elastomeric material can be attached, in a relaxed condition, to absorbent article 8 while front portion 10 and/or rear portion 14 of absorbent article 8 is pleated. Other conventional arrangements providing retractive force in the waist of absorbent article 8 are also contemplated by the invention.

Chassis 28 generally comprises outer cover 30 and bodyside liner 32. Chassis 28 can also comprise absorbent core 34, and layer 50 of cellulosic pulp.

Outer cover 30 can be formed from a single layer, or from multiple components, layers, or partial layers, of material, such that the resulting outer cover is substantially impermeable to liquids. A typical outer cover 30 may be manufactured from a thin plastic film or other flexible liquid-impermeable material. For example, outer cover 30 can be formed from a polyethylene film having a thickness of from about 0.012 millimeters to about 0.051 millimeters. When it is desirable that outer cover 30 have a more clothlike feeling, it may comprise, for example, a polyethylene film laminated to a surface of a nonwoven web, such as a spunbonded web of polyolefin fibers. For example, a polyethylene film having a thickness of about 0.015 millimeters may have thermally or otherwise laminated thereto a spunbonded web of polyolefin fibers having a thickness of from 1.5 to 2.5 denier per filament, which nonwoven web has a basis weight of about 24 grams per square meter. Further, outer cover 30 can be formed of a woven or nonwoven fibrous web which has been totally or partially constructed or treated to impart a desired level of liquid impermeability to selected regions that are adjacent or proximate absorbent core 34. Still further, outer cover 30 may optionally be composed of a micro-porous material which permits vapors to escape from absorbent core 34 and through the outer cover while preventing liquid exudates from passing through the outer cover.

Bodyside liner 32 covers absorbent core 34 in front portion 10 of absorbent article 8. Bodyside liner 32 extends into rear portion 14 of absorbent article 8. Bodyside liner 32 can be secured about the outer perimeter of, and top or body contacting side of fecal retaining structure 38 as shown in FIG. 5. Bodyside liner 32 must be impermeable to liquids at locations about and adjacent fecal retaining structure 38 so the fecal material or exudates remain within retaining structure 38.

Bodyside liner 32 must be cut or otherwise have an aperture corresponding to aperture 40 of fecal retaining structure 38. Thus bodyside liner 32 then covers the entire perimeter of fecal retaining structure 38. In this way, bodyside liner 32 functions as both a bodyside liner and storage compartment/outside wall 41 for fecal retaining structure 38.

In the embodiment shown in FIG. 7, a porous bodyside liner 32 is secured beneath fecal retaining structure 38. A separate layer of material then forms the storage compartment or wall about fecal retaining structure 38.

A suitable bodyside liner 32 may be manufactured from a wide selection of web materials, such as porous foams, reticulated foams, apertured plastic films or natural or synthetic fibers. For example, bodyside liner 32 may comprise wood or cotton fibers. Other possible materials are synthetic fibers, such as polyester or polypropylene fibers, or a combination of natural and synthetic fibers. Bodyside liner 32 is suitably utilized to help isolate the liquids held in absorbent core 34 from the skin of the wearer.

In addition, various woven and nonwoven fabrics can be used for bodyside liner 32. For example, bodyside liner 32 may be composed of a meltblown or spunbonded web of polyolefin fibers. Bodyside liner 32 may also comprise a carded and/or bonded web composed of natural and/or synthetic fibers. Bodyside liner 32 preferably comprises a substantially hydrophobic material wherein the hydrophobic material is treated with a surfactant or otherwise processed to impart a desired level of wettability and hydrophilicity in regions excluding the area about the perimeter of fecal retaining structure 38.

In a particular embodiment of the present invention, bodyside liner 32 may comprise a spunbonded polypropylene fabric composed of about 2.8–3.2 denier fibers formed into a web having a basis weight of about 22 grams per square meter and a density of about 0.06 grams per cubic centimeter. The fabric is treated with about 0.3 weight percent of a surfactant, except about and around the perimeter of fecal retaining structure 38. Bodyside liner 32 may comprise a multiplicity of components, layers, or partial layers, which correspond to any of the materials disclosed herein, as well as others known in the art.

As illustrated, absorbent core 34 is located within the front half of absorbent article 8 between central axis 20 and front edge 12. Preferably absorbent core 34 is confined within front portion 10 of absorbent article 8. At this location, as shown in FIG. 1, absorbent core 34 absorbs liquids such as, for example, urine, from the body of the user while fecal retaining structure 38 retains fecal material.

Absorbent core 34 suitably comprises a relatively thicker structure, compared to outer cover 30 and bodyside liner 32, and includes a matrix of hydrophilic fibers, such as a web of cellulosic fluff, preferably in combination with a high-absorbency material commonly known as superabsorbent material. In a particular embodiment, absorbent core 34 comprises a mixture of superabsorbent hydrogel-forming particles and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into absorbent core 34.

Alternatively, absorbent core 34 may comprise a laminate of fibrous webs and superabsorbent material or other suitable means of maintaining a superabsorbent material in a localized area.

Absorbent core 34 can have any of a number of shapes. For example, the absorbent core may be rectangular, oval-shaped or may be a pledget having two sections extending rearwardly and having a gap therebetween as shown in FIG. 1. The relatively thicker structure of absorbent core 34 generally does not extend over the entire dimensions of outer cover 30 or bodyside liner 32. Typically, absorbent core 34 is confined to front portion 10 of absorbent article 8.

While absorbent core 34 can extend under fecal retaining structure 38, typically such absorbent core has a thicker front portion, and a thinner rear portion under the fecal retaining structure. Absorbent core 34 can be cut-out where fecal retaining structure 38 is mounted. As shown in FIG. 1, absorbent core 8 can be formed as a pledget with two sections extending rearwardly and thus may be spaced somewhat from fecal retaining structure 38.

The superabsorbent material in absorbent core 34 can be selected from among natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

As shown in FIG. 1, fecal retaining structure 38 defines a perimeter which contains an aperture 40. Fecal retaining structure 38 preferably is formed by at least a first layer 42 of compressible material shown in FIG. 3 and a second layer 44 of compressible material shown in FIG. 4. The second layer 44 preferably is secured to the first layer 42 as shown in FIG. 5. Channels 46 formed in first layer 42 allow fecal material and liquids to enter cavity 48.

Fecal retaining structure 38 has a length and a width. The length of fecal retaining structure 38 generally is about 45% to about 65% of the length of absorbent article 8 at rest. The width of fecal retaining structure 38 varies, especially for the bicycle-seat shaped structure shown in FIG. 1. At least one of the first layer 42 and/or the second layer 44 generally define a perimeter wall about the entire circumference of fecal retaining structure 38 thereby defining aperture 40.

Fecal retaining structure 38 can retain at least 90 cubic centimeters of exudates. A front edge 39 of fecal retaining structure 38 typically extends from about 1.2 centimeters to about 5 centimeters frontwardly of central axis 20 into front portion 10.

First layer 42 of compressible material and second layer 44 of compressible material can comprise resiliently compressible foam materials, such as polypropylene or polyethylene having suitable compression resistance. First layer 42 generally is more rigid and less compressible than second layer 44. Having second layer 44 adjacent the body of the user, less rigid than first layer 42, provides a better physical feel to a wearer who is in contact with the second layer during normal usage. Closed cell foam material or any other material having proper compressibility can also be utilized to form fecal retaining structure 38.

First and second layers 42, 44 are typically substantially free from superabsorbent material. The resiliently compressible material forming first layer 42 and second layer 44 is typically non-pneumatic. While second layer 44 preferably is less rigid than first layer 42, absorbent article 8 can function properly when second layer 44 is more rigid or has the same compressibility as first layer 42.

In another embodiment (not shown), fecal retaining structure 38 comprises a single layer of material. The single layer has a compressibility gradient across its thickness, e.g. the part of the single layer farthest from the body of the user is more rigid than the part of the layer adjacent the body of the user.

Furthermore, while an embodiment with two layers 42, 44 is shown, multiple layers can also function properly. Therefore, the invention is not limited to only the two layers shown, or to one layer, but can comprise any number of layers.

First and second layers 42, 44 of resiliently compressible material can be formed of closed cell foam material. For example, polyethylene or polypropylene can act as the compressible material. Any other material having proper compressibility and rigidity can also be utilized to form the fecal retaining structure 38.

Figure 3:
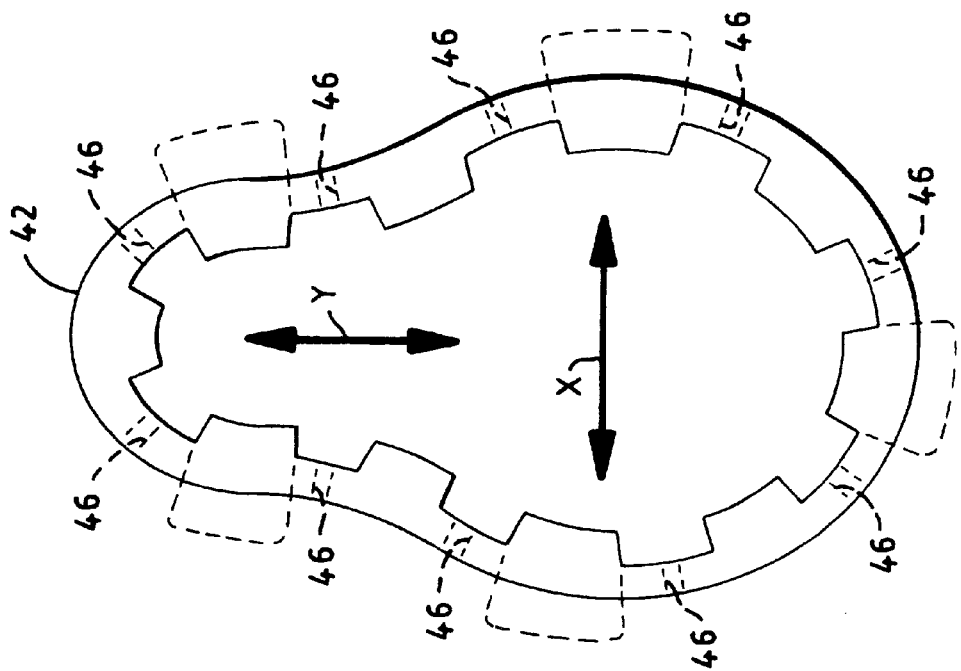
FIG. 3 shows a top view of a first layer of compressive material.

First layer 42 can have a saw tooth type of shape as shown in FIG. 3. The inner edge of first layer 42 can also have a smooth shape (not shown). While a bicycle-seat shape is shown in FIG. 3, other shapes, such as an elliptical shape or a rectangular shape with an elliptical aperture 40, as shown in FIG. 7, can function properly.

First layer 42 can also comprise a plurality of individual elements (not shown) secured to the perimeter of second layer 44. In such an embodiment, the gaps between the individual elements would generally correspond to channels 46. The individual elements would generally correspond to widened portions of first layer 42 shown in FIG. 3.

As more clearly shown in FIGS. 5 and 7, outside edge 45 of second layer 44 extends outwardly beyond first layer 42 and thus forms cavity 48 therebelow. The distance outside edge 45 of second layer 44 extends outwardly beyond first layer 42 preferably is from about 0.6 centimeters to about 2 centimeters, and most preferably from about 0.6 centimeters to about 1.2 centimeters. Having outside edge 45 of second layer 44 extend outwardly beyond first layer 42 causes fecal retaining structure 38 to collapse outwardly, if at all, to maintain openness under pressure. If fecal retaining structure 38 would collapse inwardly, aperture 40 would tend to close. Second layer 44 can extend beyond first layer 42 distances less than 0.6 centimeters. However, as the distance lessens, the ability of second layer 44 to ensure collapse outwardly, rather than inwardly, decreases.

Fecal retaining structure 38 including first layer 42 and second layer 44 preferably has an uncompressed thickness between about 1.2 centimeters and about 2.5 centimeters at rest in the z direction. Second layer 44 preferably has a minimum width of between about 1.2 centimeters and about 2.5 centimeters at the narrowest locations around its perimeter. The above range of thickness, in combination with the width of first layer 42 and especially second layer 44, maintains the structural integrity of fecal retaining structure 38 in the x and y directions during normal usage. Second layer 44 preferably extends about the entire perimeter of aperture 40 to provide sufficient structural integrity. In this manner, openness of aperture 40 is assured.

Directions x, y and z, as shown in FIGS. 3 and 5, are substantially perpendicular to one another. Direction z shows the depth of aperture 40.

Channels 46 preferably are cut or otherwise formed in first layer 42. As shown in FIG. 5, channels 46 preferably are formed in portions of first layer 42 adjacent the chassis 28 of absorbent article 8. At this location, channels 46 are as far as possible from the body of the user.

Channels 46 can also be located upward from the location shown in FIG. 5. In this instance, channels 46 can also be formed by an edge of second layer 44.

Channels 46 extend radially outwardly from aperture 40. Channels 46 preferably have a length of from about 0.6 centimeters to about 4.5 centimeters. Channels 46 preferably have a width of from about 0.6 centimeters to about 1.9 centimeters.

Channels 46 can have a rectangular shape, as shown in FIG. 5, an elliptical shape or other selected shapes. The number of channels for absorbent article 8 number from about 6 channels to 22 channels.

Figure 4:
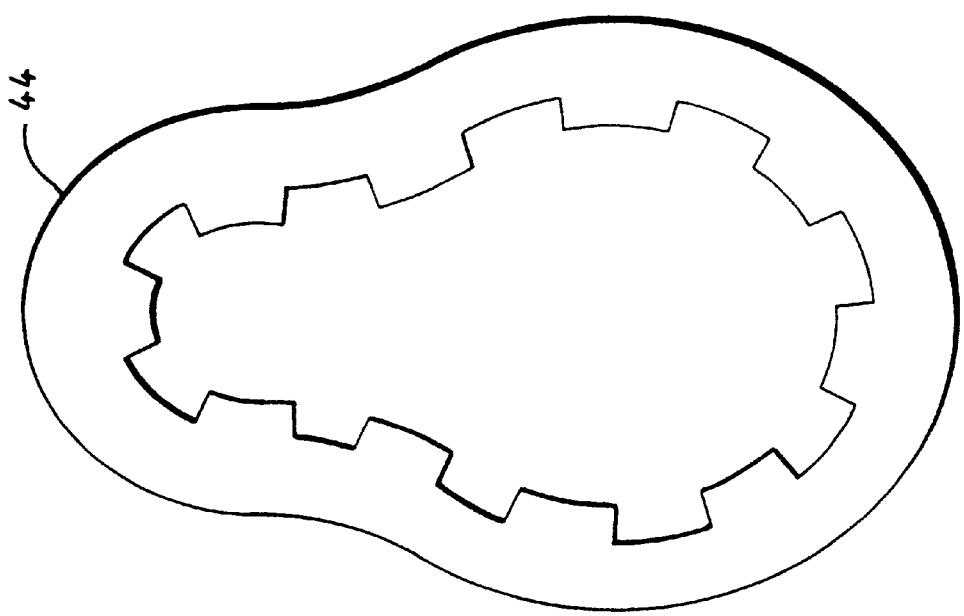
FIG. 4 shows a top view of a second layer of compressive material.

Channels 46 preferably connect to a cavity 48. Cavity 48 is formed by second layer 44 extending outwardly a greater distance than first layer 42 as shown in FIG. 5. Bodyside liner 32 effectively forms outside wall 41 of cavity 48. Exemplary relative sizes of first layer 42 and second layer 44 are shown in FIGS. 3 and 4. This arrangement increases the amount of exudates that can be stored via channels 46 by providing cavity 48. Channels 46 can communicate with each other about the perimeter by way of cavity 48.

Furthermore, by having cavity 48 extend about the circumference of fecal retaining structure 38 a greater quantity of fecal material can be stored in the aperture 40 than if cavity 48 were not present. Having cavity 48 connect with all of the channels 46 allows fecal material entering a single channel 46 to spread through the cavity and into other channels 46 if necessary.

In other embodiments, cavity 48 need not extend about the entire perimeter of retaining structure 38. Cavity 48 can be divided into a plurality of cavities or designed to provide connections between selected channels. Changing the number of cavities can be done by changing the shape of first layer 42 to project outwardly in selected locations about the same distance as second layer 44. One contemplated change in shape is shown by dashed lines in FIG. 3 extending the size of first layer 42.

Aperture 40, in combination with channels 46 and cavity 48 can receive and retain at least 90 cubic centimeters of exudates. The capacity of absorbent article 8 can vary with the overall size of absorbent article 8 which depends upon the size of the user.

A layer 50 of cellulosic pulp preferably provides a base or mounting surface for fecal retaining structure 38 as shown in FIG. 5. Layer 50 can be mounted where absorbent core 34 is cut-out, mounted to outer cover 30 as shown in FIG. 5, or mounted to bodyside liner 32 of chassis 28 as shown in FIG. 7.

Layer 50 preferably comprises uncreped through air-dried bleached chemical thermal mechanical pulp (UCTAD) that is formed by combining wood fibers with a wet strength resin in creating a higher-strength web, and drying the resulting web in what is commonly referred to as an uncreped through-drying process. Additional details regarding layer 50 are set forth in U.S. patent application Ser. No. 08/226,735 by Wendt et al entitled "Method of Making Soft Tissue Products" filed Apr. 12, 1994, the disclosure of which is hereby incorporated by reference. Other absorbent materials with suitable or similar characteristics can be used in place of cellulosic pulp.

Layer 50 of cellulosic pulp preferably has a basis weight of between about 90 and about 140 grams per square inch, and most preferably about 105 grams per square inch. Layer 50 preferably has an absorption capacity of between about 6 grams and about 10 grams of normal body liquid exudates per gram of fiber.

A preferred layer 50 has a thickness, when dry of about 0.6 millimeters. When such preferred layer 50 becomes saturated with liquid, its thickness increases to about 0.7 millimeters. The increase in thickness of the illustrated support layer 40, when saturated, is less than about 17%. Accordingly, layer 50 can absorb liquid exudates to its capacity without deleterious swelling, and accompanying closure, or effective closure, of aperture 40 by such swelling.

In contrast, a typical superabsorbent material, such as those described earlier with respect to absorbent core 34 have greater swelling when saturated with liquids. An exemplary superabsorbent pad having a thickness of 1.7 millimeters when dry, swells to 5.8 millimeters when saturated with liquid. The superabsorbent pad therefore increases in thickness by over 230%. Such an increase in thickness by layer 50 would effectively render aperture 40 inoperable, or far less efficient, for retention of fecal material. Therefore, layer 50 functions much differently than superabsorbent material.

In operation, attachment ears 22, in combination with front waist elastomeric element 24 and rear waist elastomeric element 26, secure absorbent article 8 to the body of a user. In use, fecal retaining structure 38 is seated generally on the buttocks about the anus of the user. Since fecal retaining structure 38 is made of a resiliently compressible material, the retaining structure can readily bend and flex to conform to the contours of the body of the user, as well as to movement by the user which exerts compressible and bending forces. Thus, where layers 42 and 44 are properly selected for compressibility, fecal retaining structure 38 readily conforms and adjusts to changes in the shape of the body of the user, as well as related pressures, while retaining volumetric holding capacity of at least 90 cubic centimeters, and maintaining comfortable contact with the skin of the user.

The compressibilities of layers 42 and 44 are selected in view of the typical weight of a typical user as well as in view of the size and shape of aperture 40. When so properly selected, the buttocks skin of a typical user will be spaced from the bottom of aperture 40, for example from layer 50, under all conditions of use. Thus, aperture 40, maintains an opening spacing the skin from layer 50 under all normal conditions of use.

Absorbent core 34 collects liquid such as urine passing through bodyside liner 32 in front portion 10 of absorbent article 8. Meanwhile fecal retaining structure 38 receives and retains fecal material. Fecal material in aperture 40 can enter cavity 48 via channels 46. This arrangement allows for the storage of greater amounts of fecal material. Fecal material entering channels 46 and cavity 48 is contained within the cavity by impermeable portions of bodyside liner 32 and does not contact the skin of the user, thereby providing safe and effective storage. Layer 50 of cellulosic pulp, preferably uncreped through-air dried pulp, receives and retains liquids present in the fecal material. Layer 50 of cellulosic pulp can store a significant amount of liquid without expanding significantly and reducing the volume of aperture 40.

Figure 6:
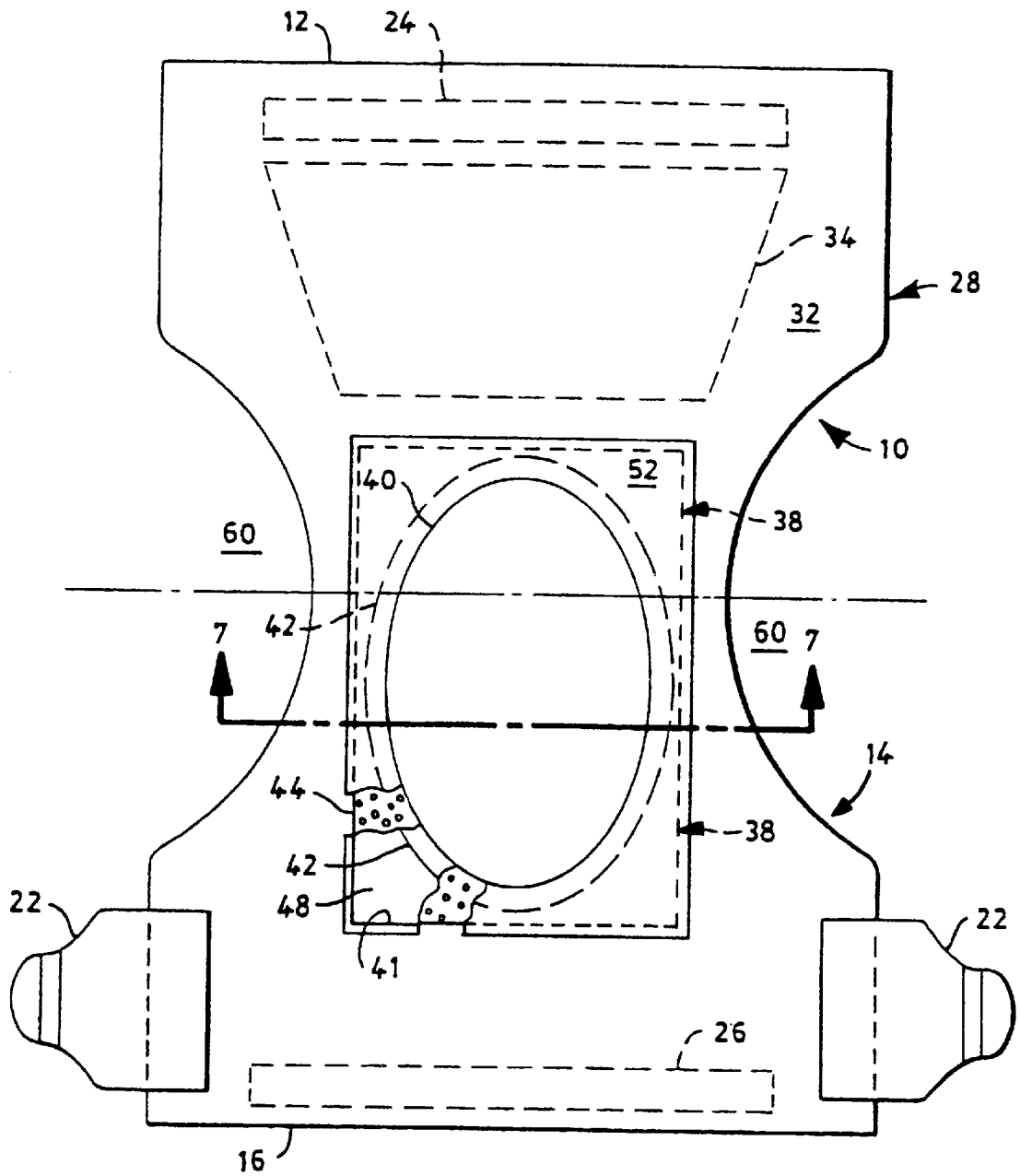
FIG. 6 shows a top view, with a partial section, of the inner or body side of another embodiment of the absorbent article.

FIG. 6 shows another embodiment of the absorbent article 8. Absorbent core 34 no longer has sections extending downward. In this embodiment, fecal retaining structure 38 is covered by an impermeable layer 52 covering first layer 42 and second layer 44 of foam material. Impermeable layer 52 preferably comprises a polyethylene film laminated to a surface of a nonwoven web, such as a spunbonded web of polyolefin fibers. This type of material has a clothlike feeling when contacted by the body of a user. Other types of materials formed of woven or nonwoven fibrous web can also be utilized for impermeable layer 52. Impermeable layer 52 can comprise a single layer, or multiple components, layers, or partial layers of material.

FIG. 7 taken at 7—7 in FIG. 6 more clearly shows the structure of the second embodiment. Channels 46 and cavity 48 receive and retain fecal material in the same manner as in the first embodiment. Impermeable layer 52 replaces bodyside liner 32 at fecal retaining structure 38 and overlays the perimeter of fecal retaining structure 38. Impermeable layer 52 retains fecal material in cavity 48. In this embodiment, cavity 48 is much larger in the corners of fecal retaining structure 38 because of its rectangular shape. Therefore, more fecal material can be stored in the embodiment of FIG. 6 than in the earlier embodiment.

While layer 50 of cellulosic pulp is shown in FIGS. 5 and 7, this layer is not required for the invention to function properly. In the embodiment of FIG. 5, layer 50 can be removed and outer cover 30 can contain fecal material in aperture 40. In the embodiment of FIG. 7, layer 50 can be replaced with a layer of impermeable material, such as that disclosed with respect to outer cover 30 or impermeable layer 52.

The bodyside liner 32, outer cover 30, absorbent core 34 and other elements disclosed herein are secured to each other by known conventional methods such as adhesives, ultrasonic bonding, sewing, or the like.

As the size of absorbent article 8 increases to fit various users, the width and length of fecal retaining structure 30 can be increased to provide more storage volume for fecal material.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

Having thus described the invention, what is claimed is:

1. An absorbent article having a length, a width, and a central axis perpendicular to the length of said absorbent article dividing said absorbent article into a front portion and a rear portion comprising:
   (a) a chassis comprising
      (i) an outer cover, and
      (ii) a bodyside liner mounted to said outer cover and adapted to contact a body of a user;
   (b) an absorbent core located between said bodyside liner and said outer cover, and
   (c) a fecal retaining structure mounted to said chassis at least in the rear portion of said absorbent article, said fecal retaining structure having at least one layer of a resiliently compressible material, defining a perimeter of said fecal retaining structure, and encompassing an aperture in said fecal retaining structure, said aperture having a bottom, said resiliently compressible material having sufficient flexibility to press and seal against the body of the user when bent during application to the body of the user, and sufficient compression resistance to maintain a space in said aperture between the body of the user and the bottom of said aperture under normal application of weight and pressure as applied by the user, said absorbent core being laterally displaced from said fecal retaining structure and said bodyside liner for separating said at least one layer and the body of the user, said bodyside liner being located about said aperture and being impermeable to liquid along said perimeter of said fecal retaining structure, so that fecal material will remain within said fecal retaining structure.

2. An absorbent article as in claim 1, wherein said resiliently compressible material is substantially free from superabsorbent material.

3. An absorbent article as in claim 1, wherein said resiliently compressible material is non-pneumatic.

4. An absorbent article as in claim 1, wherein said resiliently compressible material comprises a resiliently compressible foam material.

5. An absorbent article as in claim 1, wherein said fecal retaining structure has at least two layers of resiliently compressible material comprising a first layer having a first compressibility and a second layer, for placement adjacent the body of the user, spaced outwardly from said first layer, said second layer having a second compressibility, said first compressibility being less than said second compressibility.

6. An absorbent article as in claim 1, wherein said at least one layer extends about an entire circumference of said aperture.

7. An absorbent article as in claim 1, wherein said fecal retaining structure including channels formed in said at least one layer and extending radially outwardly of said aperture.

8. An absorbent article as in claim 1, wherein said fecal retaining structure is capable of storing at least 90 cubic centimeters of exudates.

9. An absorbent article as in claim 1, wherein said at least one layer of resiliently compressible material comprises closed cell polyethylene foam.

10. An absorbent article as in claim 1, wherein said at least one layer of resiliently compressible material comprises polypropylene foam.

11. An absorbent article as in claim 1, wherein a front edge of said fecal retaining structure extends from about 1.2 centimeters to about 5 centimeters frontwardly of the central axis and into said front portion.

* * * * *